(12) United States Patent
Desai et al.

(10) Patent No.: US 7,208,144 B2
(45) Date of Patent: Apr. 24, 2007

(54) STABILIZED DISPERSION OF BEHENYL ALCOHOL

(75) Inventors: Saurabh Desai, Somerset, NJ (US); John Goffredo, Lake Hiawatha, NJ (US); Claus Nieendick, Krefeld (DE); Amrit Patel, Dayton, NJ (US)

(73) Assignees: Cognis Corporation, Cincinnati, OH (US); Colgate-Palmolive Co., Piscataway, NJ (US)

( * ) Notice: Subject to any disclaimer, the term of this patent is extended or adjusted under 35 U.S.C. 154(b) by 547 days.

(21) Appl. No.: 10/248,012

(22) Filed: Dec. 10, 2002

(65) Prior Publication Data

US 2004/0109839 A1 Jun. 10, 2004

(51) Int. Cl.
*A61Q 5/00* (2006.01)

(52) U.S. Cl. .............................. 424/70.19; 424/70.24; 424/70.27

(58) Field of Classification Search ................. None
See application file for complete search history.

(56) References Cited

U.S. PATENT DOCUMENTS

| | | | |
|---|---|---|---|
| 4,883,660 A | 11/1989 | Blackman et al. | |
| 4,892,728 A | 1/1990 | Kawa et al. | |
| 5,100,657 A | 3/1992 | Ansher-Jackson et al. | |
| 5,510,100 A | 4/1996 | Picard et al. | |
| 5,827,920 A | 10/1998 | Watanabe et al. | |
| 5,948,416 A | 9/1999 | Wagner et al. | |
| 5,958,431 A | 9/1999 | Brancq et al. | |
| 5,973,066 A | 10/1999 | Sakuta et al. | |
| 6,200,554 B1 * | 3/2001 | Yeoh et al. | 424/70.12 |
| 6,274,130 B1 | 8/2001 | Murray | |
| 6,419,946 B1 | 7/2002 | Sonneville et al. | |
| 6,608,011 B2 * | 8/2003 | Patel et al. | 510/124 |
| 2003/0068293 A1 * | 4/2003 | Giles | 424/70.21 |

FOREIGN PATENT DOCUMENTS

| | | |
|---|---|---|
| EP | 0615741 | 9/1994 |
| EP | 0846752 | 5/1998 |
| WO | WO 02/34216 | 5/2002 |

OTHER PUBLICATIONS

International Specialty Products et al: "Prolipid (™) 131 in hair care products"; Kenneth Mason Publications, Hampshire, GB, vol. 403, No. 37 XP007122138.

* cited by examiner

*Primary Examiner*—Jyothsna Venkat
(74) *Attorney, Agent, or Firm*—John F. Daniels; Arthur G. Seifert

(57) ABSTRACT

IR 6 (Cosmetics, Toiletry and Fragrance Association, Inc., $7_{th}$ ed. 1997). Viscosities are measured using Brookfield viscometers (1,000–20,000 cps, Spindle No. 5, 20 rpm, 60 second run, 25 degrees C.) unless otherwise indicated. 967-00—IR # 6961-00-1-A low viscosity, stable dispersion of behenyl alcohol comprising: (a) 10–40 weight % on an actives basis of behenyl alcohol; (b) 1.0–8.0 weight % of an anionic surfactant selected from the group consisting of sodium lauryl ether sulfate, sodium lauryl sulfate, magnesium lauryl ether sulfate, magnesium lauryl sulfate, calcium lauryl ether sulfate, calcium lauryl sulfate, ammonium lauryl ether sulfate, and ammonium lauryl sulfate; and (c) 1.0–3.0 weight % (on an actives basis) of a betaine selected from the group consisting of C12–18 amidopropylbetaine; wherein the dispersion has a stability of at least 3 months at a temperature of 49 degrees C., a viscosity in the range of 1,000–20,000 centipoise, and no more than 0.2 weight % of cationic material.

14 Claims, No Drawings

STABILIZED DISPERSION OF BEHENYL ALCOHOL

BACKGROUND OF INVENTION

1. Field of the Invention

This invention relates to ways of stabilizing dispersions of behenyl alcohol, to create improved pearlizing compositions which can be stable at room temperature.

2. Background of the Invention

The stabilization and use of behenyl alcohol is described in a variety of references.

U.S. Pat. No. 4,892,728 to Kawa et al describes pumpable cationic fatty alcohol dispersion with a low content of cationic dispersant. The dispersion is made with 0.01–1 weight % of a cationic surfactant containing a quaternary ammonium, pyridinium or imidazolinium group and a linear C8–22 alkyl or 2-hydroxyalkyl group.

U.S. Pat. No. 4,883,660 to Blackman et al describes gel bases for pharmaceutical compositions comprising behenyl alcohol and a glycol or selected ethoxylated solvent.

U.S. Pat. No. 5,100,657 to Ansheer-Jackson et al describes hair conditioning compositions which provide cleaner hair than others based on quaternary ammonium compounds and lipid materials. The primary thickening agent is a nonionic long chain alkylated cellulose ether. A fatty alcohol such as behenyl alcohol is used as a conditioning agent.

U.S. Pat. No. 5,510,100 to Picard et al describes an oil-in-water emulsion containing an auto-emulsifiable composition based on a fatty alcohol and on an alkyl polyoside and a co-emulsifying agent.

U.S. Pat. No. 5,827,920 to Wanatabe et al describes a surfactant-free emulsion comprising a higher alcohol which is a solid at room temperature, an acrylic acid-methacrylic acid alkyl copolymer and a silicone oil.

U.S. Pat. No. 5,948,416 to Wagner et al describes stable topical compositions comprising a stable, hydrophobic, structuring agent (which can include behenyl alcohol), and a hydrophilic surfactant.

U.S. Pat. No. 5,973,066 to Sakuta et al describes an oil-in-water aqueous organopolysiloxane emulsion comprising a quaternary ammonium chloride having 1 or 2 stearyl or behenyl groups.

U.S. Pat. No. 6,274,130 to Murray et al describes a rinse off conditioning product for hair comprising a cationic surfactant, a selected emulsion polymerized dimethiconol nonionic conditioning polymer, which composition can optionally include behenyl alcohol.

U.S. Pat. No. 6,419,946 to Sonneville et al describes a nanoemulsion based on mixed esters of a fatty acid or fatty alcohol, of a carboxylic acid and of a glycerol.

Behenyl alcohol has seen a variety of uses in personal care products, particularly for hair care. It is an object of the invention to provide stabilized forms of behenyl alcohol which are useful as pearlizing agents and which are easier to use than conventional types of behenyl alcohol compositions.

SUMMARY OF INVENTION

A low viscosity, stable dispersion of behenyl alcohol comprising: (a) from about 10 to about 40 weight % on an actives basis (preferably 20–25%) of behenyl alcohol; (b) from about 1.0 to about 8.0 weight % (preferably 1–5%) of an anionic surfactant selected from the group consisting of sodium lauryl ether sulfate, sodium lauryl sulfate, magnesium lauryl ether sulfate, magnesium lauryl sulfate, calcium lauryl ether sulfate, calcium lauryl sulfate (best for avoiding viscosity problems), ammonium lauryl ether sulfate, and ammonium lauryl sulfate; (c) from about 1.0 to about 3.0 weight % (on an actives basis) of a betaine selected from the group consisting of C12–18 amidopropylbetaine (for example, cocamidopropyl betaine); (d) optionally from about 0.3 to about 5.0 weight % of a C12–C20 straight chain or iso-branched alcohol having 2–20 (particularly 2–10) moles of ethoxylation (for example, Isosteareth-2, lsosteareth-4, Isosteareth-10, Laureth 2–20, and especially Laureth-2, Laureth-4 and Laureth-10) (with higher amounts of ethoxylation being used for the longer carbon chains); and (e) optionally a cationic material having less than or equal to 22 carbons (for example, a cationic material such as a C8–22 alkyl ammonium chloride, preferably one selected from the group consisting of cetyl trimethyl ammonium chloride, (also called cetrimonium chloride) and cocotrimethylammonium chloride); wherein the dispersion: (a1) has a stability of at least 3 months at a temperature of 49 degrees C.; (b1) has a viscosity in the range of 1,000–20,000 centipoise ("cps") (for example, 1,000–20,000 cps, particularly 1,000–15,000 cps, and, more particularly, 1,000 cps–8,000 cps); and (c1) is limited to less than 0.2 weight % of total cationic material.

The invention also comprises a method for (A) combining the ingredients listed above; (B) melting and mixing the set of ingredients using a temperature in the range of about 80 to about 85 degrees C. to create a combined material; (C) stirring and homogenizing the combined material at a temperature in the range of about 80 to about 85 degrees C. for at least about an hour; (D) cooling the combined material down to a temperature in the range of about 20 to about 25 degrees C. at a cooling rate in the range of about 0.05–0.4 degrees C./minute, preferably 0.15–0.3 and, most preferably, at a rate of 0.2–0.25 degrees C./minute; and (E) holding the combined material at the temperature of about 20 to about 25 degrees C. for at least 2 hours.

DETAILED DESCRIPTION

The dispersions of the invention are shear thinning. Since the dispersion can increase in viscosity during storage, it is preferred to initially make the dispersion at the lower range of viscosity such as in the range of 1,000–5,000 cps.

By "stable" is meant that the dispersion is judged by visual observance as giving 0% separation even at temperatures in the range of 49 degrees C. for the 3 month time period described. It has been found that at least 1% of the anionic surfactant and at least 1% of the betaine are needed in order to get the superior stability described for the invention.

It is preferred to include Isosteareth-2 if a hair conditioning product is to be made since it contributes to the conditioning effect of the final hair care composition.

The behenyl alcohols included in this invention can include natural as well as synthetically made alcohol. For natural alcohol, it is understood that a distribution of carbon lengths is included. One preferred type of behenyl alcohol useful for this invention is a 72–80% material sold under the tradenames Lanette 22, Stenol 1822 A, Stenol 1822–80, and Lanette 22–80.

The alcohols are used in this invention to obtain a pearlizing effect (such as in hair care products such as shampoos, conditioners and combination products) and processability.

The use of dispersions of alcohols (especially behenyl alcohol) is helpful in keeping process costs down since the dispersion allows stable hair car products to be made with a cold process.

Viscosity is related to particle size control; during the manufacturing process the dispersion must be cooled down to at least 25, most preferably 20 degrees C. and kept at this temperature of 20–25 degrees C. for at least for 2 hours to get a good viscosity result.

The ingredients described above are commercially available.

TABLE A shows the impact on viscosity of final temperature for cooling down.

Procedure: Melt and/or mix up all the ingredients listed for the specific Example. Heat the mixture up to a temperature in the range of 80–85 degrees C. Stir/homogenize the material for 1 hour and then start to cool down with a cooling rate of 0.2–0.25 degrees C./min. Viscosity was measured 24 hours after manufacturing/finishing the compound with Brookfield equipment, RVT, 25 C, Spindle 5, 20 rpm.

TABLE A

| Ingredient | Ex. 1A | Ex. 2A | Ex. 3A |
|---|---|---|---|
| Water | QS | QS | QS |
| Sodium Lauryl 2EO Sulfate | 6.0 | 6.0 | 6.0 |
| Cocamidopropyl betaine | 1.0 | 1.0 | 1.0 |
| Laureth-4 | 1 | 1 | 1 |
| Behenyl alcohol | 25.0 | 25.0 | 25.0 |

Cooled-down to 30° C. 25,000 mpas Cooled down to 25° C. 15,000 mpas Cooled down to 25° C. and 5000 mPascals kept 2 hours at 25degrees C. It is preferred to have the combination of Isosteareth-2 and Betaine. Also, when fatty alcohol ethoxylates are ethoxylates are used, the maximum amount should preferably be kept to 2%, for example, between 1–2%,

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for viscosity, molecular weights and degree of ethoxylation or propoxylation are averages. Temperatures are in degrees C. unless otherwise indicated. As is true for the rest of the application as well, the amounts of the components are in weight percents based on the standard described; if no other standard is described then the total weight of the composition is to be inferred. Various names of chemical components include those listed in the CTFA International Cosmetic Ingredient Dictionary Example A General Method To the main mixing vessel is added water and the anionic surfactant (such as sodium laureth sulfate). The mixture is stirred with heating to a temperature of 80–85 degrees C. Then the pH is adjusted to pH 7–8. After this adjustment the alkylamidopropylbetaine and the nonionic surfactant are added while maintaining the temperature is at 80–85 degrees C. When addition of the surfactant is completed the behenyl alcohol is added in molten liquid (such as Lanette-22 (72–80%) or slowly in solid state so that the temperature is maintained at 80–85 degrees C. The contents of the mixing vessel are stirred for at least 45–60 minutes at 80 to 85 degrees C. Next the vessel is cooled down at a cooling rate of 0.05–0.4 degrees C./minute, preferably 0.1 5–0.3 and, most preferably, at a rate of 0.2–0.25 degrees C./min. After the mixture is cooled to about 20–25 degrees C. the specifications are checked. The mixture is then stirred for another 1–2 hours at 20–25 degrees C. Viscosity may be measured, if desired, using the equipment and conditions described above.

Examples 1–15

The General Method described in Example A may be used to make 5 kg size batches using the types and amounts of ingredients listed in Tables B–D. Examples 1–6 are comparative examples to show formulations outside of the invention.

TABLE B

Single Surfactant Systems

| Ingredient | Ex. 1 | Ex. 2 | Ex. 3 | Ex. 4 | Ex. 5 | Ex. 6 |
|---|---|---|---|---|---|---|
| Water | QS | QS | QS | QS | QS | QS |
| Sodium Lauryl 2EO Sulfate | 1.0 | 8.0 | 0 | 0 | 0 | 0 |
| Cocamidopropyl betaine | 0 | 0 | 2.0 | 4.0 | 0 | 0 |
| Cetrimonium chloride | 0 | 0 | 0 | 0 | 0.80 | 5.0 |
| Behenyl alcohol | 10.0 | 40.0 | 10.0 | 30.0 | 10.0 | 40.0 |
| Total | 100 | 100 | 100 | 100 | 100 | 100 |

Viscosity measurements were: Example 1: non-homogeneous, lumpy, 100 mpas Example 2: sticky paste, lumpy, >100000 mpas Example 3: non-homogeneous, lumpy, 100 mpas Example 4: non-homogeneous, lumpy, 200 mpas Example 5: non-homogeneous, lumpy, 1000 mpas Example 6: paste, lumpy thick, white cream>100000 mpas

TABLE C

Multiple Surfactant Systems With Isosteareth-2

| Ingredient | Ex 7 | Ex 8 | Ex 9 | Ex 13 | Ex 14 |
|---|---|---|---|---|---|
| Water | QS | QS | QS | QS | QS |
| Sodium Pareth 2EO Sulfate | 0 | 0 | 0 | 0 | 4.0 |
| Sodium Lauryl 2EO Sulfate | 2.0 | 4.0 | 1.0 | 2.5 | 0 |
| Cocamidopropyl betaine | 1.0 | 2.0 | 1.0 | 1.0 | 0 |
| Cetrimonium chloride | 0 | 0 | 0.5 | 0.2 | 0 |
| Isosteareth-2 | 2.0 | 1.0 | 0.5 | 0.5 | 2.0 |
| Behenyl alcohol | 25.0 | 25.0 | 25.0 | 25.0 | 25.0 |
| Laureth 1–10 | 0 | 0 | 0 | 1.0 | 0 |
| Total | 100 | 100 | 100 | 100 | 100 |
| Stability | stable | stable | unstable | borderline | unstable |

TABLE D

Multiple Surfactant Systems Without Isosteareth-2

| Ingredient | Ex 10 | Ex 11 | Ex 12 | Ex 15 |
|---|---|---|---|---|
| Water | QS | QS | QS | QS |
| Sodium Lauryl 2EO Sulfate | 4.0 | 0.5 | 0.5 | 3.0 |
| Cocamidopropyl betaine | 1.0 | 0.5 | 0.25 | 3.0 |
| Behenyl alcohol | 25.0 | 15.0 | 25.0 | 25.0 |
| Laureth 1–10 | 2.0 | 1.0 | 4.0 | 0 |
| Total | 100 | 100 | 100 | 100 |
| Stability | stable | unstable | unstable | stable |

What is claimed is:

1. A low viscosity, stable aqueous dispersion of behenyl alcohol comprising:

(a) about 10–40 weight % on an active basis of behenyl alcohol;
(b) about 1.00–8.0 weight % of an anionic surfactant selected from the group consisting of sodium laurel ether sulfate, sodium laurel sulfate, magnesium lauryl ether sulfate, magnesium lauryl sulfate, calcium laurel ether sulfate, calcium laurel sulfate, ammonium lauryl ether sulfate, and ammonium lauryl sulfate;
(c) about 1.0 to 3.0 weight % on an active basis of a betaine selected from the group consisting of C12–18 amidopropylbetaine;
(d) optionally, about 0.3–5.0 weight % of a C12–C20 straight chain or iso-branched alcohol having 2–20 moles of ethoxylation; and
(e) optionally, a cationic material having ≦22 carbon atoms; wherein the dispersion
   (a1) has a stability of at least 3 months at a temperature of 49 degrees C.;
   (b1) has a viscosity in the range of 1,000–15,000 centipoise; and
   (c1) is limited to less than 0.2 weight % of total cationic material.

2. A low viscosity, stable aqueous dispersion of behenyl alcohol according to claim 1, comprising
(a) about 20–25 weight % on an active basis of behenyl alcohol; and
(b) about 1–5 weight % of an anionic surfactant.

3. A low viscosity, stable aqueous dispersion of behenyl alcohol according to claim 1, having a viscosity in the range of 1,000–8,000 centipoise.

4. A low viscosity, stable aqueous dispersion of behenyl alcohol according to claim 1, wherein the betaine is cocoamidopropyl betaine.

5. A low viscosity, stable aqueous dispersion of behenyl alcohol according to claim 1, wherein the anionic surfactant is sodium lauryl sulfate.

6. A low viscosity, stable aqueous dispersion of behenyl alcohol according to claim 1, wherein the C12–C20 straight chain or iso-branched alcohol having 2–20 moles of ethoxylation is present and is selected from the group consisting of isosteareth-2, isosteareth-4, isosteareth-10, and Laureth 2–20 alcohols.

7. A process for making a low viscosity, stable aqueous dispersion of behenyl alcohol having a stability of at least 3 months at a temperature of 49 degrees C., a viscosity in the range of 1,000–8,000 centipoise; and less than 0.2 weight % of total cationic material, the process comprising
(A) combining a set of ingredients comprising
   (a) about 10–40 weight % on an active basis of behenyl alcohol;
   (b) about 1.00–8.0 weight % of an anionic surfactant selected from the group consisting of sodium laurel ether sulfate, sodium laurel sulfate, magnesium lauryl ether sulfate, magnesium lauryl sulfate, calcium laurel ether sulfate, calcium laurel sulfate, ammonium lauryl ether sulfate, and ammonium lauryl sulfate;
   (c) about 1.0 to 3.0 weight % on an active basis of a betaine selected from the group consisting of C 12–18 amidopropylbetaine; and
   (d) optionally, about 0.3–5.0 weight % of a C12–C20 straight chain or iso-branched alcohol having 2–20 moles of ethoxylation;
(B) melting and mixing the set of ingredients using a temperature in the range of 80–85 degrees C to create a combined material;
(C) stirring and homogenizing the combined material at a temperature in the range of 80–85 degrees C. for at least an hour;
(D) cooling the combined material down to a temperature in the range of 20–25 degrees C. at a cooling rate in the range of 0.05–0.4 degrees C./minute; and
(E) holding the combined material at a temperature of 20–25 degrees C. for at least two hours.

8. A low viscosity, stable aqueous dispersion of behenyl alcohol produced according to the process of claim 7.

9. A low viscosity, stable aqueous dispersion of behenyl alcohol comprising:
(a) about 20–25 weight % on an active basis of behenyl alcohol;
(b) about 1.00–8.0 weight % of an anionic surfactant selected from the group consisting of sodium laurel ether sulfate, sodium laurel sulfate, magnesium lauryl ether sulfate, magnesium lauryl sulfate, calcium laurel ether sulfate, calcium laurel sulfate, ammonium lauryl ether sulfate, and ammonium lauryl sulfate;
(c) about 1.0 to 3.0 weight % on an active basis of a betaine selected from the group consisting of C12–18 amidopropylbetaine;
(d) about 0.3–5.0 weight % of a C12–C20 straight chain or iso-branched alcohol having 2–20 moles of ethoxylation; and
(e) optionally, a cationic material having ≦22 carbon atoms; wherein the dispersion
   (a1) has a stability of at least 3 months at a temperature of 49° C.;
   (b1) has a viscosity in the range of 1,000–15,000 centipoise; and
   (c1) is limited to less than 0.2 weight % of total cationic material.

10. A low viscosity, stable aqueous dispersion of behenyl alcohol according to claim 9, having a viscosity in the range of 1,000–8,000 centipoise.

11. A low viscosity, stable aqueous dispersion of behenyl alcohol according to claim 9, wherein the betaine is cocoamidopropyl betaine.

12. A low viscosity, stable aqueous dispersion of behenyl alcohol according to claim 9, wherein the anionic surfactant is calcium lauryl sulfate.

13. A low viscosity, stable aqueous dispersion of behenyl alcohol according to claim 9, wherein the C112–C20 straight chain or iso-branched alcohol having 2–20 moles of ethoxylation is selected from the group consisting of one or more of isosteareth-2, isosteareth-4, isosteareth-10, and Laureth 2–20 alcohols.

14. A low viscosity, stable aqueous dispersion of behenyl alcohol according to claim 9, wherein the C12–C20 straight chain or iso-branched alcohol having 2–20 moles of ethoxylation comprises isosteareth-2.

* * * * *